(12) United States Patent
Johnson

(10) Patent No.: US 10,413,833 B2
(45) Date of Patent: Sep. 17, 2019

(54) SYSTEM AND METHODS FOR MANAGING THE PARTICIPATION OF ATHLETES IN ORGANIZED SPORTS

(71) Applicant: Compete Safe, Inc., Foothill Ranch, CA (US)

(72) Inventor: John M. Johnson, Foothill Ranch, CA (US)

(73) Assignee: Compete Safe, Inc., Foothill Ranch, CA (US)

( * ) Notice: Subject to any disclaimer, the term of this patent is extended or adjusted under 35 U.S.C. 154(b) by 80 days.

(21) Appl. No.: 15/380,244

(22) Filed: Dec. 15, 2016

(65) Prior Publication Data

US 2018/0169527 A1 Jun. 21, 2018

(51) Int. Cl.
| | |
|---|---|
| A63F 13/35 | (2014.01) |
| A63F 13/79 | (2014.01) |
| A63F 13/335 | (2014.01) |
| G16H 10/60 | (2018.01) |

(52) U.S. Cl.
CPC ............ *A63F 13/79* (2014.09); *A63F 13/335* (2014.09); *A63F 13/35* (2014.09); *G16H 10/60* (2018.01)

(58) Field of Classification Search
USPC .......................................................... 463/29
See application file for complete search history.

(56) References Cited

U.S. PATENT DOCUMENTS

| | | | | |
|---|---|---|---|---|
| 6,461,162 | B1 * | 10/2002 | Reitman ............. | G06F 19/3481 434/118 |
| 8,540,560 | B2 * | 9/2013 | Crowley ............ | A63B 24/0062 463/4 |
| 9,378,380 | B1 | 6/2016 | Reid et al. | |
| 9,378,657 | B1 * | 6/2016 | Nusbaum ............... | G09B 19/00 |
| 2005/0171787 | A1 | 8/2005 | Zagami | |
| 2007/0070429 | A1 | 3/2007 | Hein, III | |
| 2012/0029666 | A1 * | 2/2012 | Crowley ............ | A63B 24/0062 700/91 |
| 2012/0035449 | A1 * | 2/2012 | Coifman .............. | A61B 5/0871 600/365 |
| 2013/0218310 | A1 * | 8/2013 | Johnson ................. | G06F 17/60 700/91 |
| 2014/0006045 | A1 | 1/2014 | Wund, II | |

(Continued)

OTHER PUBLICATIONS

PCT Notification of Transmittal of the International Search Report and the Written Opinion of the International Searching Authority, or the Declaration, International Searching Authority, International Application No. PCT/US2017/066002, dated Jun. 22, 2018, 24 pages.

*Primary Examiner* — Pierre E Elisca

(74) *Attorney, Agent, or Firm* — Cesari and McKenna, LLP

(57) ABSTRACT

A system enables registration of individual athletes who wish to compete in organized sports leagues or other competitions. Once registered, an athlete presents an identification card which is used by the system to ensure that the athlete is not currently suspended from competition before being permitted to compete in a particular event. The system enables athletes to safely compete in multiple sports or multiple competitions sanctioned by different organizations. The system is capable of maintaining both health-related and performance-related information for each athlete while providing appropriate confidentiality and secure access.

19 Claims, 14 Drawing Sheets

(56) References Cited

U.S. PATENT DOCUMENTS

| | | | |
|---|---|---|---|
| 2014/0039651 A1* | 2/2014 | Crowley | G06Q 30/02 700/91 |
| 2014/0081436 A1* | 3/2014 | Crowley | A63B 24/0062 700/91 |
| 2014/0122866 A1 | 5/2014 | Haeger et al. | |
| 2015/0269331 A1 | 9/2015 | Bolanos et al. | |
| 2016/0220864 A1 | 8/2016 | Hollins | |
| 2017/0021228 A1* | 1/2017 | Crowley | G06Q 30/02 |
| 2017/0084196 A1* | 3/2017 | Nusbaum | G09B 19/00 |

* cited by examiner

Form
*Complete the form below and preview your results to the right.*

Upload Photo* ☒ Upload —— 302

*Please upload your photo by clicking on the UPLOAD button, then BROWSE to select your photo (JPG or TIF formats ONLY)*

First Name: Last Name:
DOB:
Club:

Weight:
Address1:
Address2:
City: State: Zip:

Badge is good for 1 year and will auto-renew provided all fees and certifications are in good standing.

300

304

[LEAGUE OR ASSOCIATION IDENTIFIER]

[PHOTO]

[NAME]

Badge Expiration Date:

FIG. 3

SYSTEM AND METHODS FOR MANAGING THE PARTICIPATION OF ATHLETES IN ORGANIZED SPORTS

BACKGROUND OF THE INVENTION

Field of the Invention

The present invention relates generally to the field of sports competitions and, more specifically, to a system for registering athletes and managing the participation of such athletes in organized competitions so as to ensure compliance with applicable health and safety protocols.

Background Information

As a result of increased public awareness and concern regarding athletes who participate in contact sports, many state and local governments, sports leagues, and sports sanctioning authorities have adopted or are considering adopting new health and safety protocols. Many such protocols are specifically directed to particular types of injuries, such as concussion, and require particular steps to be followed beginning with a suspicion that an injury has occurred and ending with a clearance for the athlete to return to competition.

While adoption of new health and safety protocols, particularly by state governments for application to their respective public school systems, has gained momentum over the past few years, this has created a growing need for reliable ways to actually comply with the protocols. There are many parties who may be partly responsible for compliance including organizers of competitions, coaches, trainers, physicians, parents, and the athletes themselves. In addition, when an athlete wishes to compete in multiple sports or wishes to compete in events which are sanctioned by different entities, considerable compliance challenges arise due to a lack of availability of current, essential information regarding the athlete's status and fitness. In at least a few documented cases, such lack of information led to fatality where an athlete who had sustained an injury in one competition was improperly allowed to participate in another.

SUMMARY OF THE INVENTION

In accordance with one aspect of the invention, a system enables registration of individual athletes who wish to compete in organized sports leagues or other competitions. Once registered, an athlete presents an identification card which is used by the system to ensure that the athlete is not currently suspended from competition before being permitted to compete in a particular event. The system enables athletes to safely compete in multiple sports or multiple competitions sanctioned by different organizations. The system is capable of maintaining both health-related and performance-related information for each athlete while providing appropriate confidentiality and secure access.

The registration process may include collection of a variety of information such as the athlete's name, address, date of birth, club or team affiliation, and photograph. Once all required registration information is submitted, a record is stored in a database or other appropriate data structure. The records may be stored in a cloud-based or other storage system with appropriate network connectivity. In addition, a permanent identification card, whose authenticity may be ensured by a variety of technologies, is prepared and delivered to the athlete. Authentication of the identification card may include an indelible and virtually indestructible invisible mark which may be read only by a preselected optical scanner installed on a smartphone, tablet or other device. If necessary, a temporary identification credential may be issued in electronic or other form with appropriate authenticity protection.

When an athlete's identification card is scanned, this triggers a query to the system's registered athlete database in real-time via a telecommunications network (wireless or wired), internet, or other suitable network. A response from the database reveals the real-time medical status of an athlete and his or her eligibility to compete. For those sports involving frequent physical contact, such as football, soccer and field hockey, an athlete may be required to present his or her identification card for scanning at each and every practice as well as formal competitions. For other sports, such as swimming or volleyball where contact and injuries are less common, an athlete might be required to present his or her identification card only at formal competitions.

At any time subsequent to completion of registration, additional information regarding the athlete, either health-related or performance-related, may be added to or associated with the athlete's record within the system. For example, if a particular protocol requires an athlete to complete a baseline concussion test prior to competition, the system may associate with the athlete's record an indication that the baseline test was completed, but not actually store the test results. Instead, if access to the baseline test is later needed because the athlete has been injured, the system may enable the baseline test result to be securely retrieved from one entity (a testing company) and routed to another entity (a hospital where the athlete has been admitted). Alternatively, performance-related information such as race times, finish positions, scores and the like may also be associated with the athlete's record in a way that an interested member of the public may access such non-confidential information by way of a "public application" running on a smartphone, tablet or other device. The public application may also be used by a scorekeeper, judge or other official to enter competition results. Similarly, a wide variety of other data sets which may be of interest to researchers, vendors of sports equipment, or other entities may be compiled by the system and made accessible by authorized users.

In order for an athlete to be allowed to participate in a given competition, he or she must have previously registered as summarized above and must present his or her identification card (via physical or digital display on smart device) at a practice or competition venue. By scanning the identification card of each would be participant, the system enables organizers of sports competitions to accurately identify each athlete and reliably confirm that such athlete is not currently suspended from competition due to injury (or possibly for a non-injury related reason). Further, re-scanning of the athlete's identification card at various designated points of a competition venue ensures that each participating athlete completes a pre-competition physical, weigh-in, staging, and post-competition evaluation as applicable.

For pre-competition physicals and other event-side activities which involve physicians or possibly other health care professionals, a "physician application" running on a smartphone, tablet or other device enables real time entry of vital signs, initial injury assessments, and other health-related information. The physician application gives an event-side physician full access to all health-related information maintained in the system which is associated with an athlete whose identification card was scanned. The physician application enables the event-side physician to report an injury in real-time, and may include a capability for recording dictation as well as alphanumeric information entered from a keyboard. The physician application may also include a capability for uploading video of an athlete's performance to the system and associating such video with the athlete's record. The physician application may also include a mechanism for immediately suspending an athlete from competition based on an event-side diagnosis or health and safety protocol requirement. Once suspended, an athlete may only be cleared to return to competition by appropriate input by a physician or other authorized person using the physician application.

A third application, an "administrator application", is also supported by the system. The administrator application is reserved for authorized personnel who are responsible for maintaining the system.

In addition to maintaining a history of an athlete's medical state, i.e., clearance or no-clearance status to compete, the system maintains a unique identification system across three entities: an overseer reporting an injury to an athlete; a test provider which administered a baseline test to the athlete; and the athlete's health care provider (HCP). By requiring a minimum of at least one unique identification data point from each entity, the system sets rules in accordance with HIPAA and FERPA requirements, allowing rules-based access to the files pertinent to each entity. When an athlete's health information is transferred between baseline test providers, primary care physicians, first responders, hospitals, and any other entity involved in the athlete's care, the system maintains HIPAA and FERPA compliance while automating delivery of all information to the HCP and the test provider for analysis and diagnosis.

To illustrate how the system may control access to and delivery of health-related information, assume that an athlete is injured during competition. An event-side physician, using the physician application, reports the injury which, in turn, causes the system to generate a unique incident identifier (incident ID). If the athlete's system record indicates that he or she was previously administered a baseline test (e.g., a concussion baseline test), the system transmits the incident ID to the test provider who administered that baseline test for possible follow-up and subsequent tests. In response, the test provider returns to the system a unique baseline identification (baseline ID), but not the test results or any other information. The system then transmits both the incident ID and baseline ID to the athlete's HCP (e.g., primary care physician, hospital emergency room, or other authorized entity).

The athlete's HCP, having received both the baseline ID and the incident ID, may now submit to the system a unique case identifier (case ID). Through the system, the test provider transmits to the HCP, as an encrypted file or other secure container, the baseline test results for the athlete. The system is able to route the test results to the correct HCP by using the baseline ID and incident ID which accompany the results. Thus, the system has the ability to transport, but not access or store, test results or other sensitive health-related information. Once received by the athlete's HCP, the baseline ID, incident ID, and case ID may be used together decrypt or otherwise gain access to the test results.

The system also provides sufficient flexibility to readily accommodate emerging technologies, new or different government mandates, and new service providers who add value with respect to athlete health and safety. For example, additional service providers who may be integrated into the system include background check providers, training material providers, academic eligibility overseers, ecommerce providers, booking and scheduling entities, equipment providers, government health agencies, sanctioning bodies, as well as amateur and professional leagues who administer eligibility oversight for specific sports.

BRIEF DESCRIPTION OF THE DRAWINGS

The invention description below refers to the accompanying drawings, of which:

FIG. 3 is a representation of an on-line screen in a public application which may be used to register an athlete with the participation management system, and a representation of a permanent identification card which is generated upon completion of registration, in accordance with one aspect of the invention;

DETAILED DESCRIPTION OF ILLUSTRATIVE EMBODIMENTS

Figure 1:
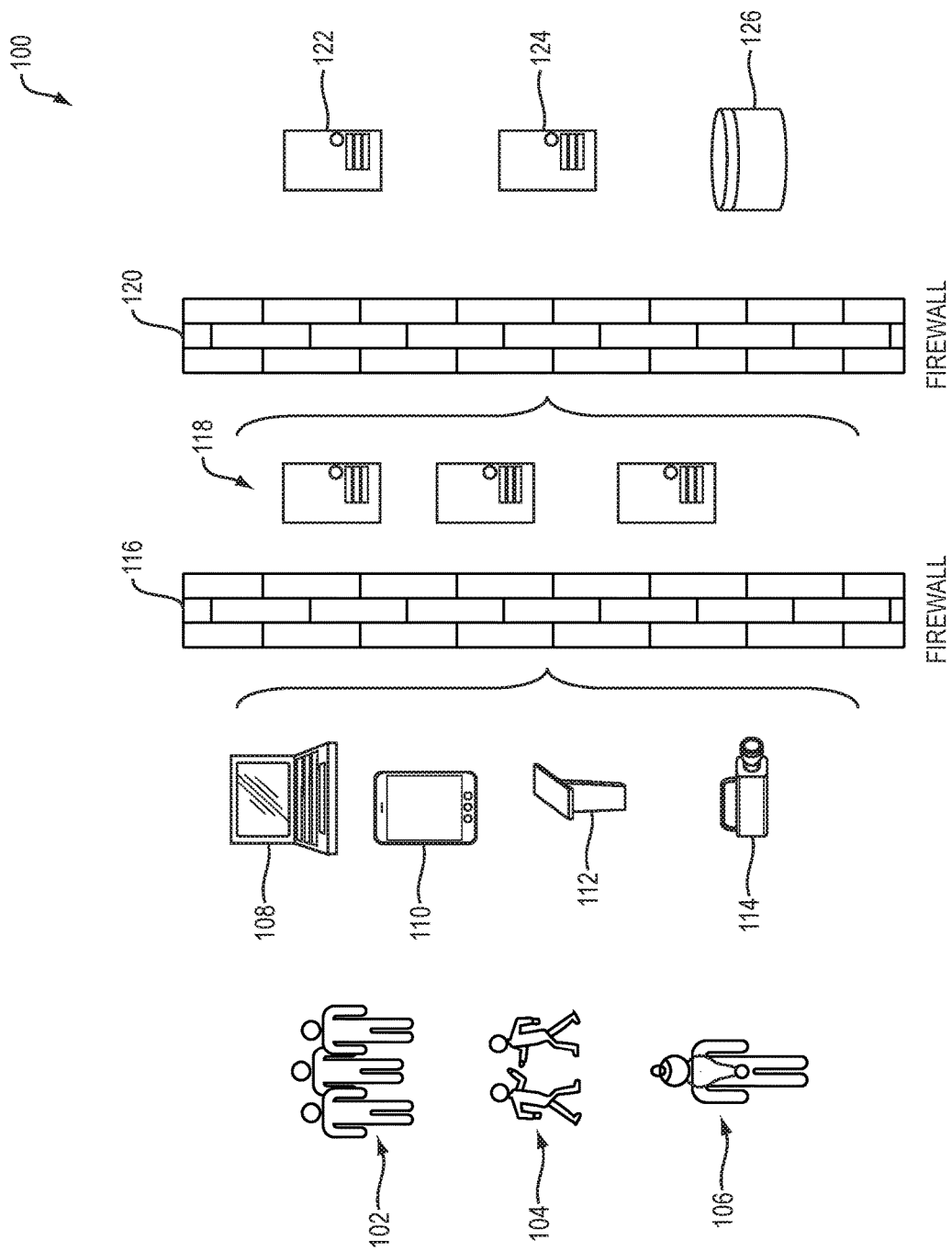
FIG. 1 is a block diagram of a cloud-based system for managing the participation of athletes in organized sports, in accordance with one aspect of the present invention.

FIG. 1 shows a cloud-based system 100 for managing the participation of athletes in organized sports. Users of system 100 may include interested members of the public 102, which are typically friends and families of athletes 104 who have registered with system 100, as described below, or simply fans of a given sport. Physicians or other health care providers (HCPs) 106 may also be users of system 100. System administrators (not shown) are also users of system 100.

Access to system 100 may be provided by a variety of devices including computers 108, smartphones and tablets 110, kiosks 112, and video cameras 114. Through a firewall 116, users, in accordance with their respective privileges as specified by a system administrator or system configuration, may interact with servers 118 to perform a variety of tasks including athlete registration, reporting an injury to an athlete, suspending an athlete from competition, clearing a suspended athlete to return to competition, or simply reviewing an athlete's won-loss record, times, or other performance-related data. For enhanced security, servers 118 are isolated, by way of a second firewall 120, from servers 122 and 124, as well as mass storage 126. As described in detail below, a user's interaction with system 100 may be facilitated through one of three applications running on a desired device: a public application; a physician application; and an administrator application.

Figure 2:
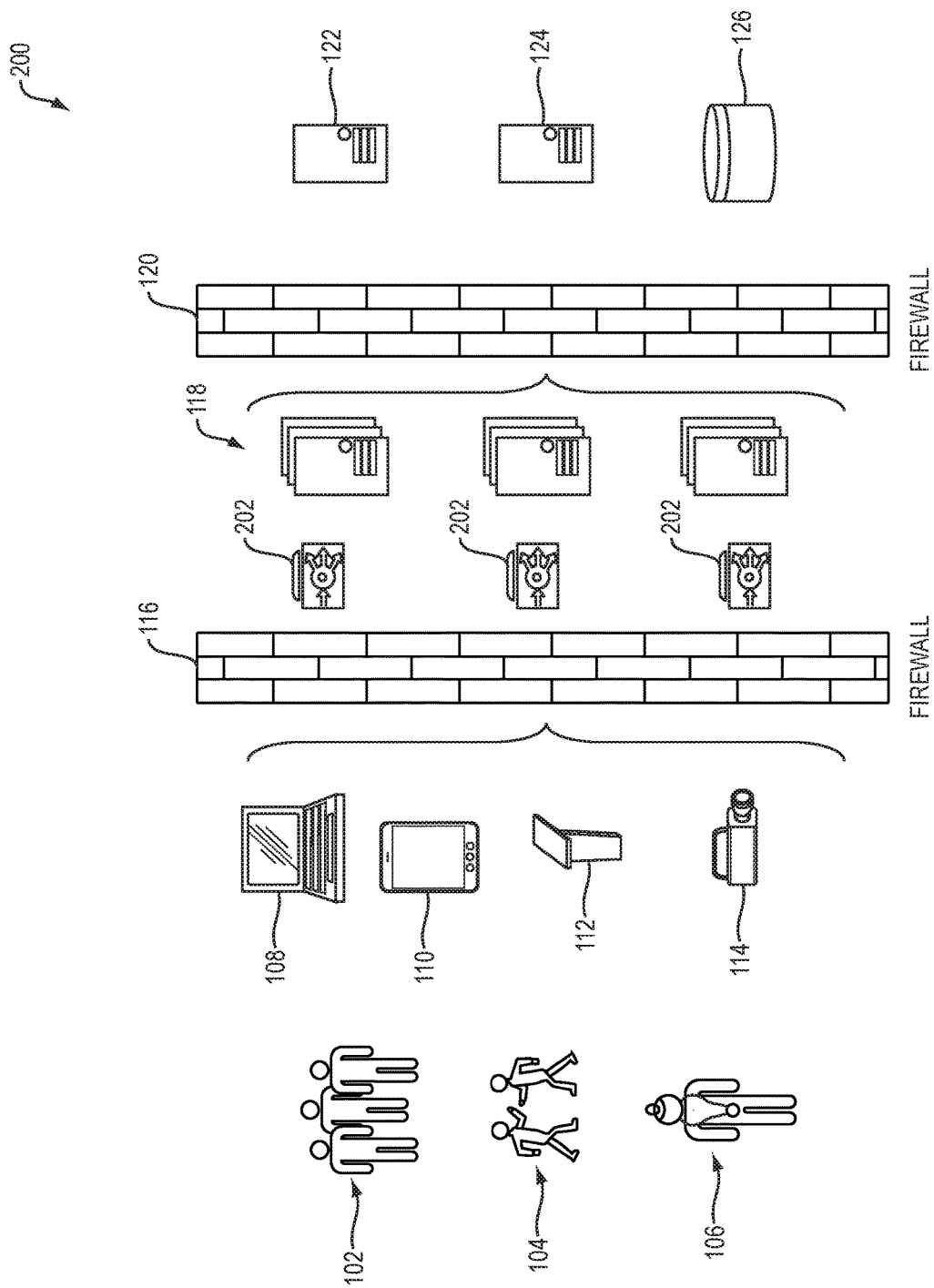
FIG. 2 is a block diagram of a cloud-based system similar to that of FIG. 1 with the addition of load balancers.

FIG. 2 shows a cloud-based system 200 which, like system 100, is for managing the participation of athletes in organized sports. For enhanced clarity, similar components or elements introduced earlier retain the same reference numbers throughout the drawings and specification except where otherwise indicated. System 200 includes load balancers 202 which may operate in a conventional manner to distribute loads, representing user activity, across available resources of servers 118, thus reducing latency and improving overall user experiences. References in this specification to system 100 should be understood to include system 200 except where otherwise indicated.

FIG. 3 shows a representation of an on-line screen 300 which may be used to register an athlete with the participation management system. An athlete, parent, or guardian enters the athlete's first and last names, date of birth (DOB), weight, home address, city, state and ZIP code in the spaces provided. By clicking on an "Upload Photo" button, a popup box will appear which enables browsing for a desired file containing a recent photograph of the athlete. Once all required alphanumeric information has been entered and a photo uploaded, a record of the athlete's registration is stored (e.g., on one of servers 118, 122, 124, or mass storage 126) along with a unique athlete ID. The athlete ID may be created in a variety of ways including a technique offered by Digimarc Corp. which combines a number and a unique pixel print record.

A preview image 304 of the athlete's permanent identification card is rendered within screen 300. As shown in preview image 304, each permanent identification card displays a league or sports association identifier or logo, the athlete's photo and name, and an expiration date.

Each permanent identification card, which may be approximately the size of a bag tag, may be fabricated at a central facility from which the cards are mailed or otherwise delivered to the now registered athletes. To both authenticate an identification card and prevent counterfeits, a digital watermark may be embedded in the athlete's photograph. Digimarc Corp. is one supplier of such digital watermark technology, as well as a software-based scanner for reading such watermarks. The software-based scanner is similar to a passport hologram reader and, once downloaded to a smartphone or other device with a camera, is essentially ready to use immediately.

Figure 4:
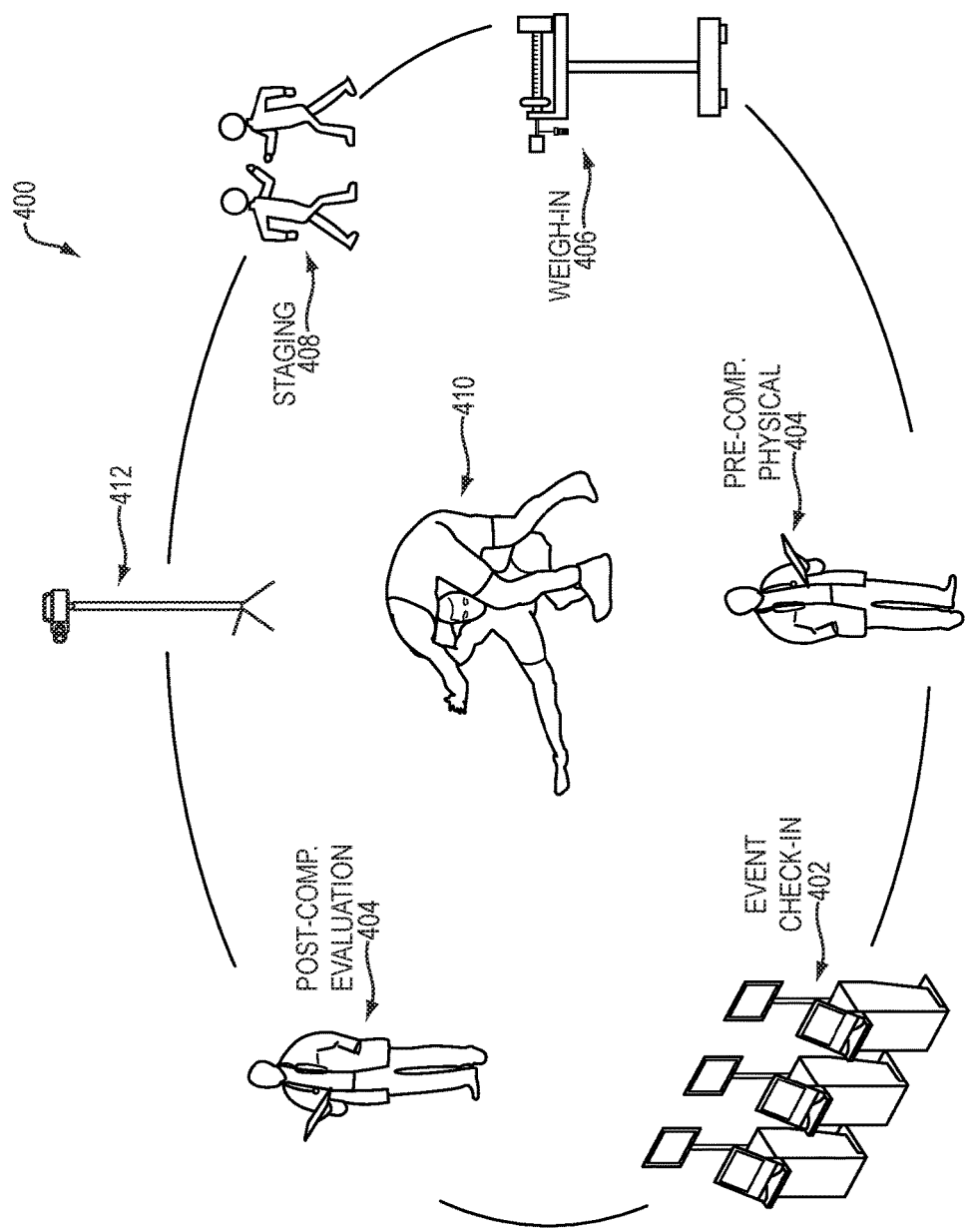
FIG. 4 is a schematic diagram illustrating various points within a competition venue at which an athlete's identification card may be scanned, and health-related or performance-related information regarding the athlete entered into a participation management system, in accordance with one aspect of the invention.

Once an athlete has completed registration and thus created a record stored within system 100, additional health-related or performance-related information regarding that athlete may be added to or associated with the athlete's record by authorized users of the system. For example, as shown in FIG. 4, at a single event 400 (e.g., wrestling meet), an athlete's identification card may be scanned multiple times each corresponding to a different health and safety check. First, upon arrival at the venue, each athlete scans his or her identification card at an event check-in kiosk 402. This scan is intended to identify any prospective competitor who (a) is currently suspended and thus ineligible to compete, or (b) has not previously registered and should be diverted for on-the-spot registration or possibly declared ineligible for the current event.

Next, each identification card is scanned again by an event-side physician 404 who is responsible for pre-competition physicals. This card scan, in conjunction with the physician's application which is described in detail below, enables event-side physician 404 to view the athlete's health history to the extent it has been previously uploaded to system 100, to enter vital signs and other observations, and to suspend an athlete for a health-related reason. Assuming that the athlete passes his or her pre-competition physical, he or she moves on to a weigh-in 406. Here again, the athlete's identification card is scanned, but this scan may be in conjunction with the public application, which may be used by a meet official to enter the athlete's current weight which is not traditionally considered confidential health information in organized sports.

Following weigh-in 406, each athlete proceeds to a staging area 408. Again the athlete's identification card may be scanned, in conjunction with the public application, as part of establishing initial matches within weight classes or similar administrative activity.

An event side video camera 412 may be positioned to record video of the competition. Through available Wi-Fi or similar connectivity, such video may be automatically uploaded to system 100, encrypted and stored. In the event of an injury, such video may be retained at least until the injured athlete is cleared to return to play as described below.

Following a match 410, each athlete's identification card is scanned again by event-side physician 404 in connection a post-competition evaluation. Similarly, a scorekeeper or other official may also scan the card again in order to enter the results of the match, or other performance data specific to the athlete.

Scanning of the identification cards described herein may be advantageously extended to practices or other organized activities as desired or as mandated by government action, insurance policies, or other factors. The face of the identification card display only an athlete's name, photo, and league or association identifier, and no further information about the athlete may be obtained without an approved scanner. This helps protect the athlete from predatory individuals who may be involved in sports competitions and eliminates the majority of theft or impersonation risk. A lost or stolen identification card has little value and is unlikely to attract thieves. If desired, an electronic backup copy of the identification card may be stored on an athlete's smartphone on a permanent or temporary basis.

Figure 5:
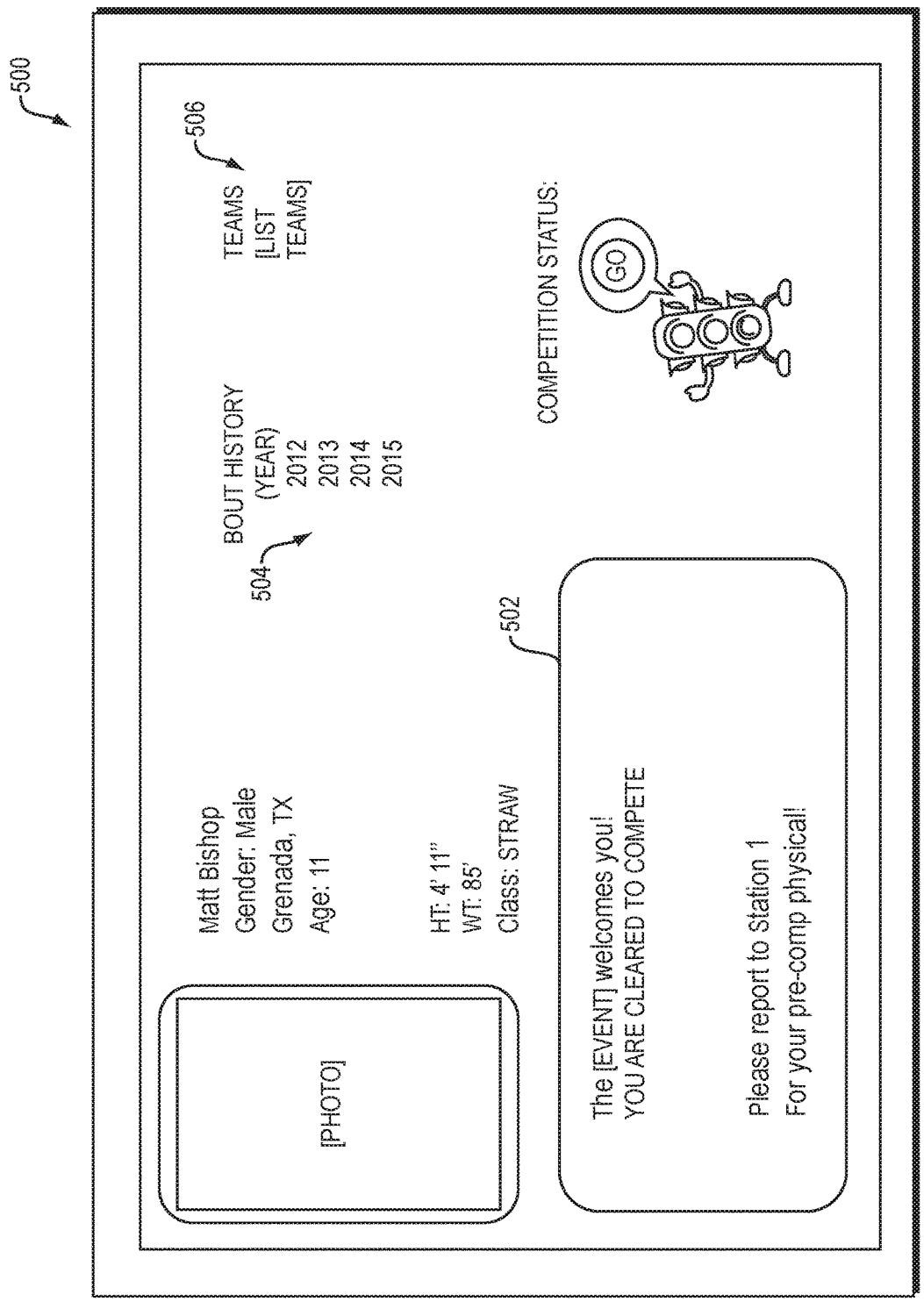
FIG. 5 is a representation of an on-line screen in a public application showing, in response to scanning an athlete's identification card, that the athlete is clear to compete along with references to the athlete's prior competition information, in accordance with one aspect of the invention.

FIG. 5 shows a representation of an on-line screen 500 which may appear in response to scanning an athlete's identification card at an event check-in. For example, screen 500 may appear at event check-in kiosk 402 (FIG. 4) when system 100 (FIG. 1), in response to a scan of an identification card, determines that the athlete whose card was scanned is clear to compete 502 in a particular sport. Because system 100 is capable of managing an athlete's participation across multiple (i.e., all) sports, it is possible for an athlete to be clear to compete in some sports but not others. Screen 500 includes displays links 504 to past results for the athlete, as well as a list of teams 506 for which the athlete has previously or is currently competing.

Figure 6:
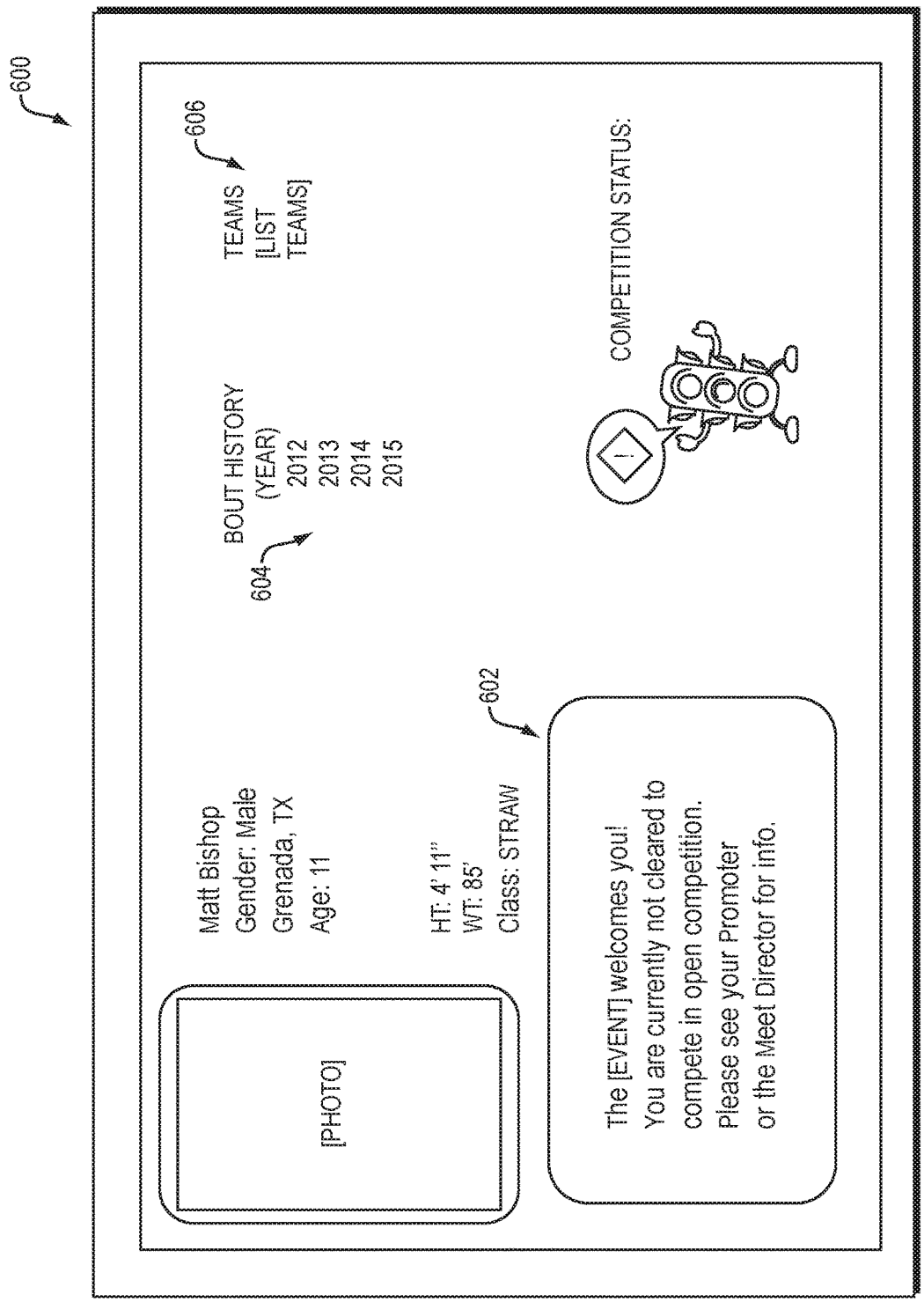
FIG. 6 is a representation of an on-line screen in a public application showing, in response to scanning an athlete's identification card, that the athlete is not clear to compete and should report to a competition authority, along with references to the athlete's prior competition information.

Alternatively, if at event check-in kiosk 402 an identification card is scanned and system 100 determines that the athlete is not clear to compete, a screen such as screen 600 in FIG. 6 may appear. A message 602 informs the athlete of his or her competition status and gives direction to see the Promoter or Meet Director for further information. Here again, screen 600 includes links 604 to past results for the athlete, as well as a list of teams 606 for which the athlete has previously or is currently competing.

Figure 7:
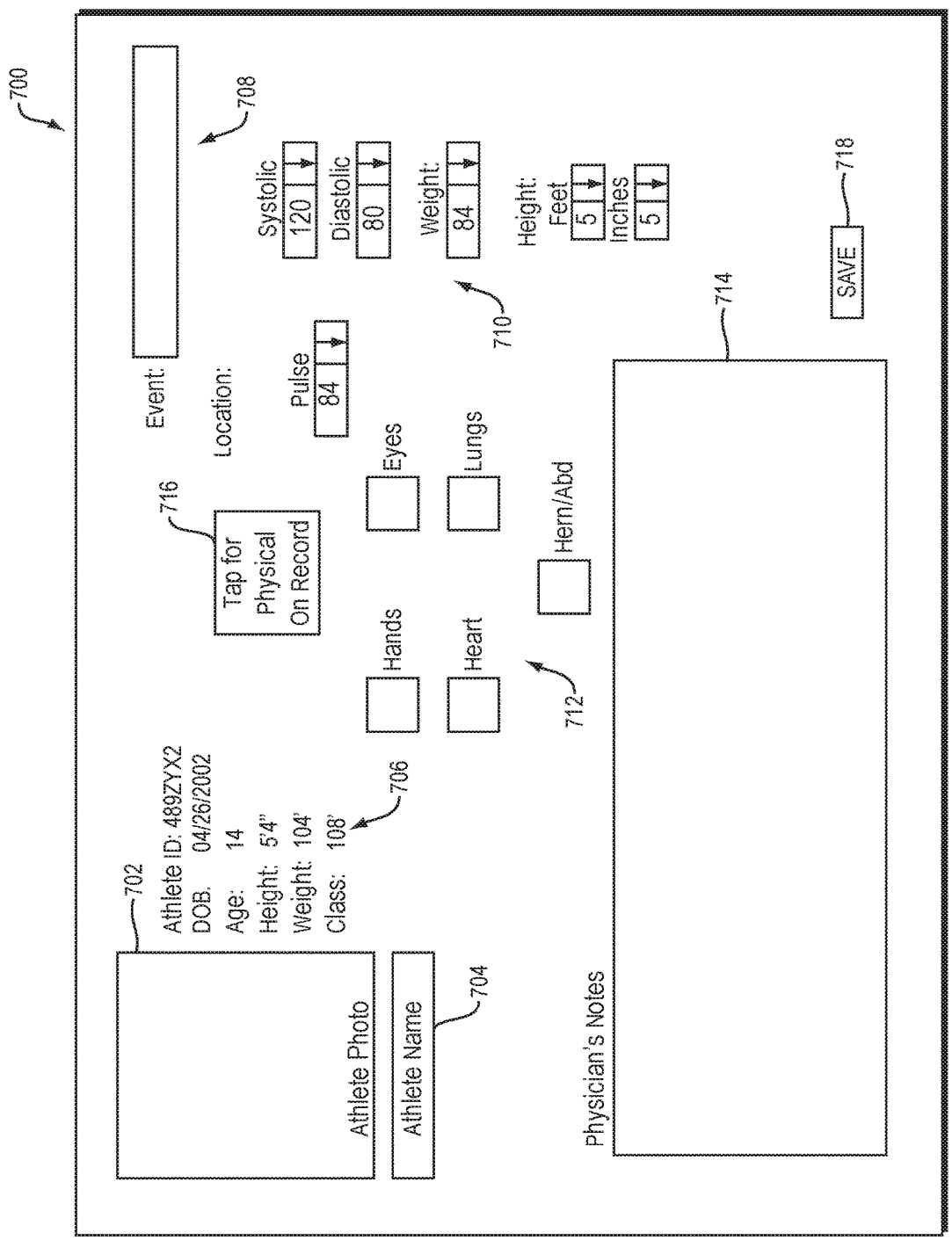
FIG. 7 is a representation of an on-line screen in a physician's application which may be used by an event-side physician to enter vital signs and other observations during a pre-competition physical or weigh-in, in accordance with one aspect of the invention.

FIG. 7 shows a representation of a screen 700 which may appear in a physician's application in connection, for example, with a pre-competition physical given by event-side physician 404 (FIG. 4). In response to a scan of an athlete's identification card, screen 700 displays the athlete's photo 702, name 704, and other basic, self-explanatory information stored in or associated with the athlete's record in system 100. Screen 700 also displays an event name and location 708.

In addition, screen 700 provides pull-down menus 710 for event-side physician 404 to enter blood pressure, weight, height, and pulse. Also, check boxes 712 are provided for event-side physician to indicate that no problem was observed regarding the athlete's hands, eyes, heart, lungs, or hernia/abdomen. A large text box 714 is provided should event-side physician 404 wish to record an observation of any kind. By clicking a button 716, event-side physician 404 may also review the athlete's previous physical if it was previously uploaded to system 100. Once event-side physician 404 has completed his or her pre-competition physical and entered all desired information, he or she clicks a save button 718, thereby uploading all information to system 100 which adds it to or associates it with the athlete's record.

Figure 8:
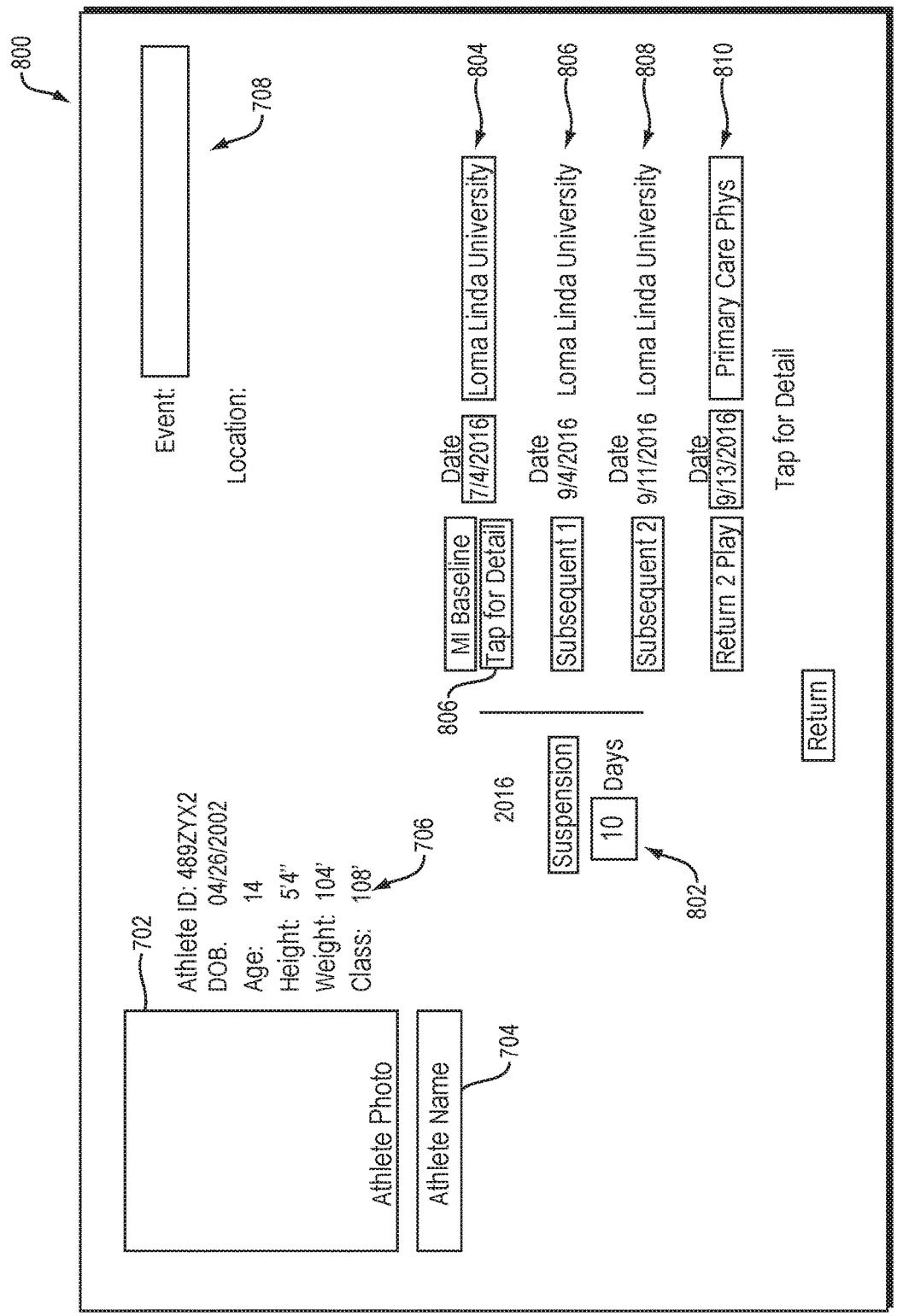
FIG. 8 is a representation of an on-line screen in the physician's application which shows an athlete's suspension history and provides links to prior test results including baseline test results for the athlete, in accordance with one aspect of the invention.

FIG. 8 shows a representation of a screen 800 which may appear in a physician's application in connection with a pre-competition physical given by event-side physician 404 (FIG. 4). Screen 800 shows that the athlete was suspended for 10 days in 2016 due to an injury. Test information 804 indicates that the athlete was administered a baseline test (e.g., baseline concussion test) by Motion Intelligence (MI), one of several current competitors offering such testing, on Jul. 4, 2016 at Loma Linda University. If event-side physician 404 wishes to review the details of the baseline test, he or she may tap button 806. The baseline test results will be made available to the event-side physician 404 as described below, but are not actually stored within system 100.

Test information 806 indicates that the athlete was administered a first, subsequent to baseline concussion test on Sep. 4, 2016, which it may be inferred was the date of the injury that caused the suspension. Test information 808 indicates that the athlete was administered a second, subsequent to baseline test on Sep. 11, 2016. Finally, return to play information 810 indicates that the athlete was cleared to compete on Sep. 13, 2016 by the athlete's primary care physician.

Figure 9:
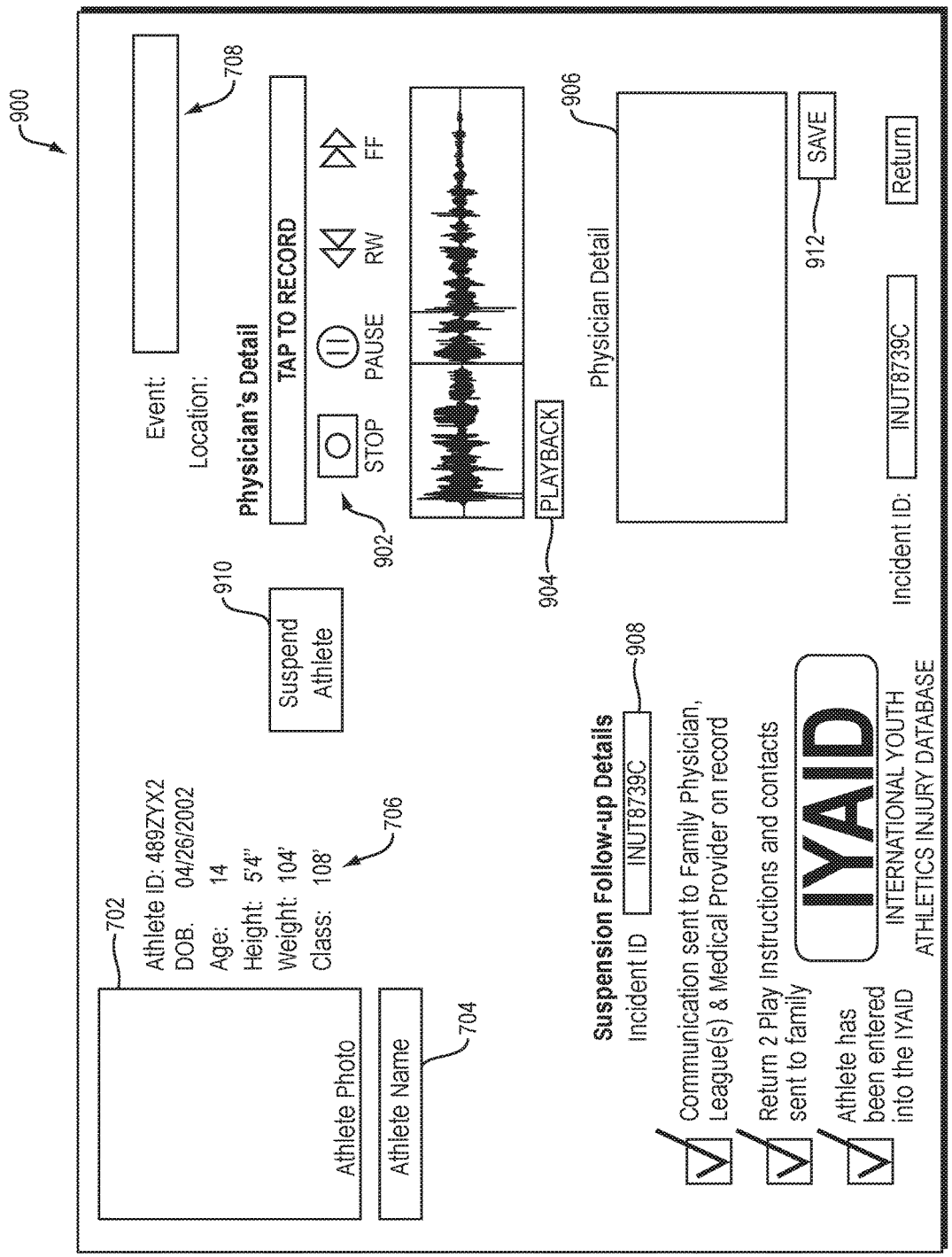
FIG. 9 is a representation of an on-line screen in the physician's application which an event-side physician may use to report an injury to an athlete as well as suspend an athlete from competition, in accordance with one aspect of the invention.

FIG. 9 shows a representation of a screen 900 which may appear in the physician's application, and which event-side physician 404 may use to report an injury to an athlete as well as suspend an athlete from competition. Using dictation controls 902 and 904, event-side physician 404 may dictate observations and findings regarding an injury that has occurred in competition. Any physician dictation is immediately encrypted and stored in system 100 in a quarantined, highly secure directory maintained among the servers or mass storage of system 100 which may only be accessed by an athlete's HCP as described below. In addition, a text box 906 enables event-side physician 404 to record written observations and findings in addition, or as an alternative, to dictation. Once event-side physician 404 has completed entry of all observations and findings, he or she clicks on save button 912, thereby saving all information to system 100.

When an injury is reported through screen 900 or an alternative input, system 100 (FIG. 1) responds, in part, by generating a unique incident ID 908. In addition, system 100 automatically transmits notifications regarding the reported injury to the athlete's family physician, league, medical provider, and overseeing body, to the extent such information was previously uploaded to system 100 and associated with the athlete's record. Similarly, system 100 automatically transmits to the athlete's family instructions to follow to seek return to play clearance (e.g., what follow-up tests are required) and appropriate contacts (e.g., which facilities are available for follow-up tests). In addition, system 100 automatically reports the injury and incident ID 908 to the International Youth Athletics Injury Database.

Should event-side physician 404 determine that the injury is sufficiently serious to warrant suspending the athlete from competition (and possibly practice), a suspend athlete button 910 is available on screen 900. Clicking button 910 will result in display of screen 1000 shown in FIG. 10, which event-side physician 404 uses to enter details regarding the injury and suspension.

Figure 10:
FIG. 10 is a representation of an on-line screen in the physician's application which an event-side physician may use to enter specific information regarding an injury that resulted in suspension of the athlete, in accordance with one aspect of the invention.

Turning now to FIG. 10, a pull-down menu 1010 enables event-side physician 404 to retrieve his or her own physician profile stored in system 100. Pull-down menu 1010 presents a list of physicians who are authorized to serve as event-side physicians or in other capacities during competitions. With screen 1000 displayed, event-side physician 404 scans the injured athlete's identification card using, for example, a smartphone camera and previously installed scanner as described above. This results in display of the injured athlete's photo 702, name 704, and basic information 706.

Check boxes 1002 permit event-side physician 404 to indicate whether the injured athlete sustained a knockout (KO) or technical knockout (TKO). Similarly, check boxes 1004 permit event-side physician 404 to specify a type of injury, while text box 1008 permits a detailed description of the injury. Pull-down menus 1006 permit event-side physician to specify a suspension period (in days) as well as a no contact period (in days). Once all information has been entered, event-side physician 404 clicks save button 1012, thereby saving all information to system 100.

Figure 11:
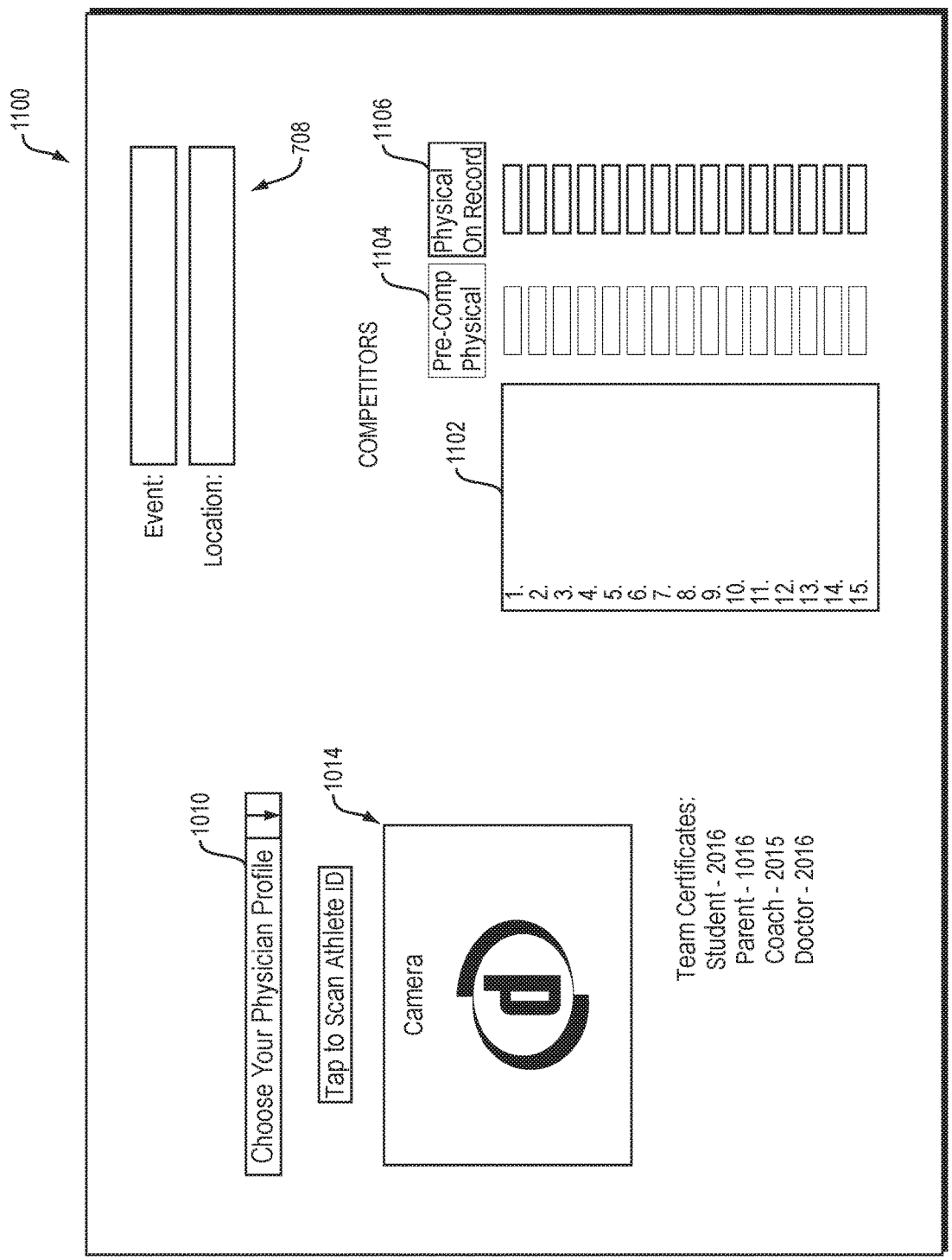
FIG. 11 is a representation of an on-line screen in the physician's application showing a list of athletes who intend to compete in a particular event along with indications of whether each such athlete has completed a pre-competition physical and had a previous physical, in accordance with one aspect of the invention.

FIG. 11 shows a screen 1100 which may appear in the physician's application for use by event-side physician 404. An athlete's identification card may be scanned by event-side physician 404, resulting in the addition of the athlete's name to a list of competitors 1102. For each athlete that appears on list of competitors 1102, there is an indicator 1104 whether that athlete has completed a pre-competition physical. Similarly, there is an indicator 1106 whether that athlete has a previous physical of record in system 100. Thus, list of competitors 1102, in conjunction with indicators 1104 and 1106, enables event-side physician 404 to immediately determine which athletes are ready to move forward toward competition and which are not yet fully eligible.

Figure 12:
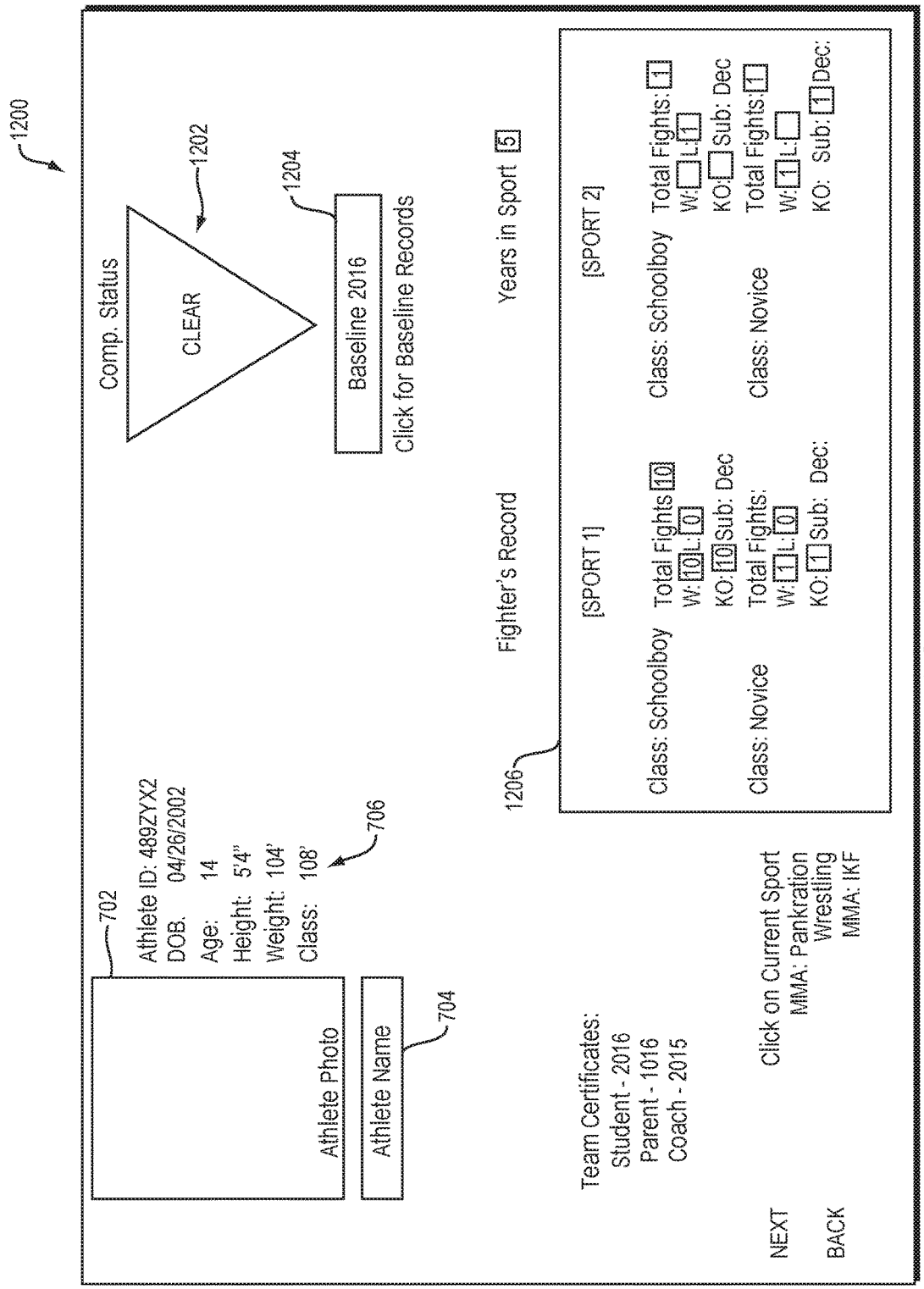
FIG. 12 is a representation of an on-line screen in a public application which may be used by an interested member of the public to access performance-related information regarding one or more athletes competing in a particular event, in accordance with one aspect of the invention.

FIG. 12 shows a screen 1200 which may appear in a public application which may be used by an interested member of the public to access performance-related information regarding one or more athletes competing in a particular event. A competition status indicator 1202 shows that the athlete is clear to compete. A baseline records button 1204 may be clicked to access the athlete's detailed performance-related data such as won-loss record, race times, orders of finishes, and similar publicly available data that was previously uploaded to system 100. A summary records box 1206 displays certain performance-related information for the athlete from competition in two sports.

Figure 13A:
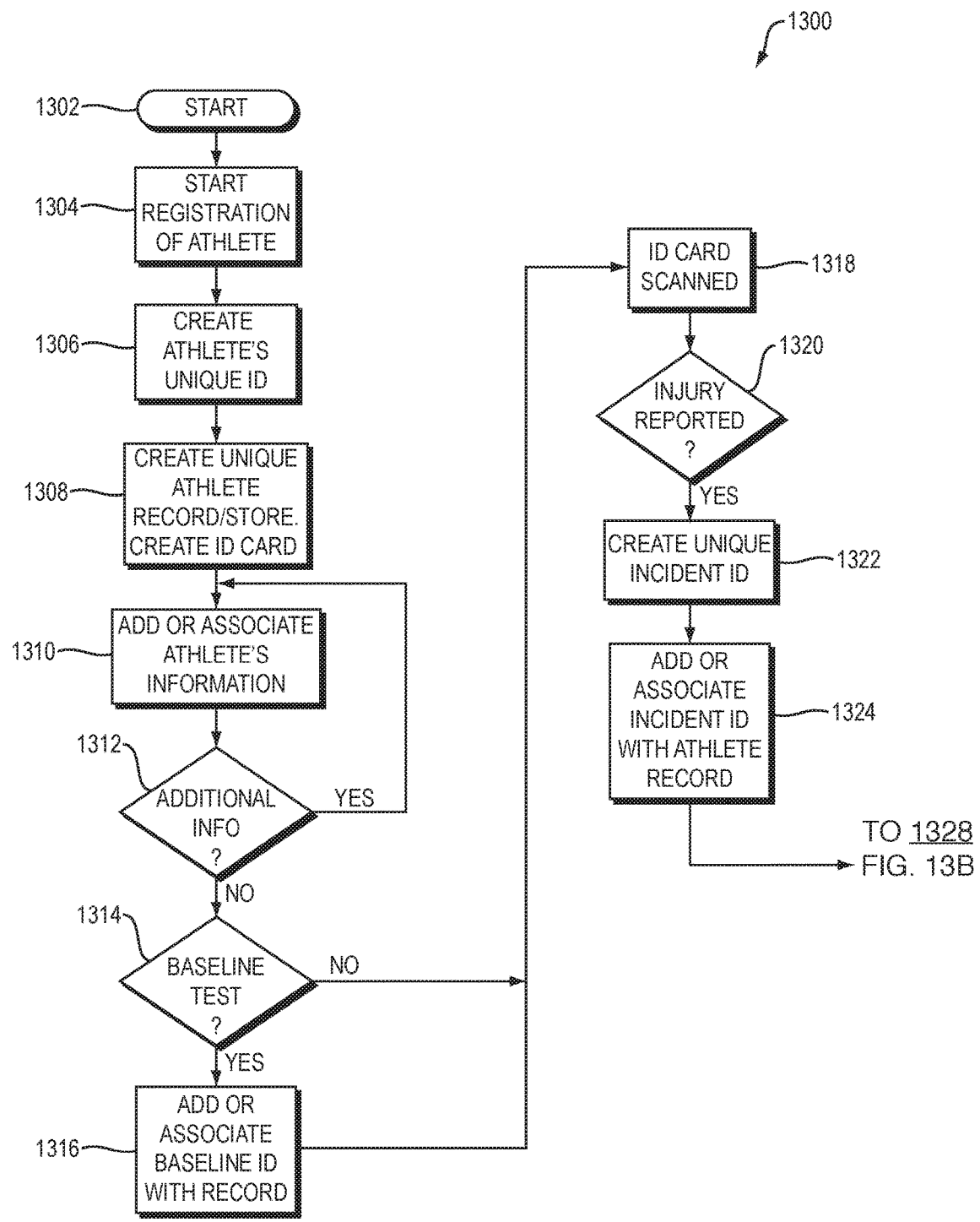
FIGS. 13A and 13B are a flowchart illustrating a method by which the participation management system may be used to provide an injured athlete's health care provider confidential access to sensitive health-related information including test results held by third party testing companies, in accordance with one aspect of the invention.
Figure 13B:
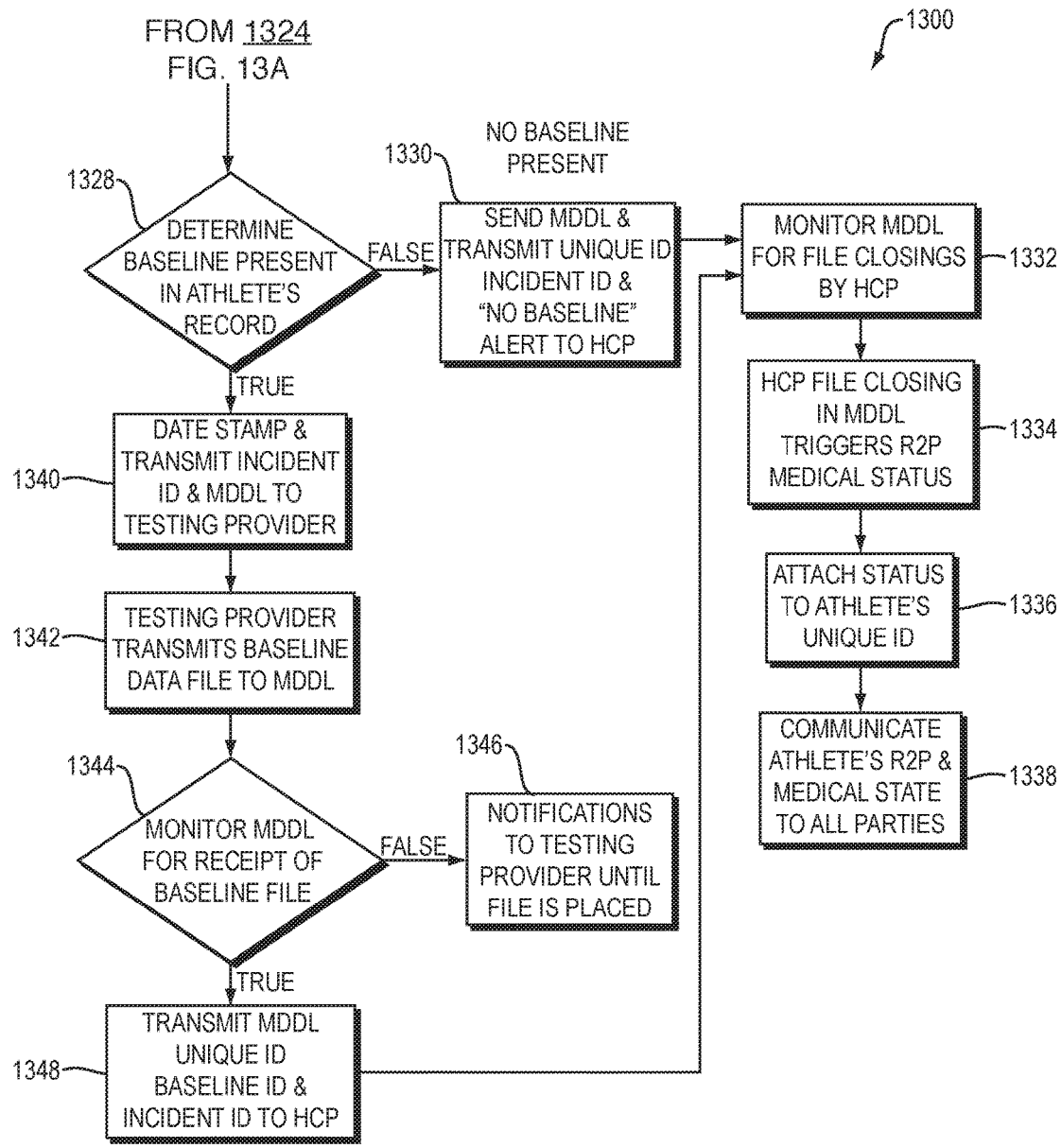

FIGS. 13A and 13B are a flowchart which illustrates a method 1300 by which system 100 may be used to enable an injured athlete's health care provider confidential access to sensitive health-related information, including test results held by third party testing companies. The method starts at step 1302 which is followed by the start 1304 of the registration process for an athlete, as described in detail above. The athlete's unique ID is created at step 1306. Subsequently, at step 1308, a unique record for the athlete is created and stored in system 100, and the athlete's permanent identification card is created.

Next, at step 1310, additional information (e.g., performance-related information) for the athlete may be added to or associated with the previously stored athlete's record. At step 1312, a determination is made whether there is any remaining additional information to be added or associated with the athlete's record. If so, the method returns to step 1310. If not, the method advances to step 1314 where a determination is made whether a baseline test (e.g., baseline concussion test) was previously administered to the athlete. If so, the method advances to step 1316 at which a unique baseline ID, which is a unique identifier but not the actual baseline test results, is obtained from a third party testing company which administered the baseline test and added or associated with the athlete's record. The baseline ID may be a unique alphanumeric string or something more complex but should, at a minimum, provide unique identification of the testing company and a specific test result that company possesses. If, at step 1314, it is determined that no baseline test was previously administered, the method bypasses step 1316.

At step 1318, a previously registered athlete's identification card is scanned. As described above, this scan may occur at a practice, competition, or other activity where it is desirable to identify each participant and confirm that he or she is not currently suspended. Next, at step 1320, a determination is made that an injury is being reported. As described above, a unique incident ID is created at step 1322, which is followed by adding or associating the incident ID with the athlete's record at step 1324.

Continuing to FIG. 13B, at step 1328, a determination is made whether a baseline test result exists for the injured athlete. If so, the method advances to step 1340 at which system 100 creates a date-stamped message which includes the incident ID and information regarding the location of a medical data destination location (MDDL). The MDDL is a quarantined, highly secure directory maintained among the servers or mass storage of system 100 which may only be accessed by the injured athlete's HCP as described below. The date-stamped message is transmitted by system 100 to the testing provider which possesses the baseline test result of interest.

Next, at step 1324, the testing provider transmits an encrypted file containing the baseline test result of interest to the MDDL within system 100. At step 1344, a process within system 100 monitors activity at the MDDL. If an expected file is not received by the MDDL by a predetermined time, system 100 will send notifications at step 1346 to the testing provider until the file is received. If, at step 1344, it is determined that the expected file has been received, the method advances to step 1348 at which system 100 transmits a message to the injured athlete's HCP. That message includes information regarding the location of the MDDL, athlete's ID, baseline ID, and incident ID. Only by possessing all three IDs contained in that message is the HCP able to gain access (e.g., decrypt and read or copy) to the file which contains the injured athlete's baseline test results.

With reference again to step 1328, if it is determined that the athlete's record does not indicate that a baseline test was previously administered, the method advances to step 1330 at which system 100 transmits a message to the injured athlete's HCP. That message includes information regarding the location of the MDDL, athlete's ID, incident ID, and an alert that no baseline test result is available through system 100. The method then advances to step 1332.

At step 1332, a process within system 100 monitors activity at the MDDL for file closings initiated by the injured athlete's HCP. A file closing by an injured athlete's HCP is the mandatory in order for the athlete to be cleared to return to play. Before a file may be closed, the HCP may be required to answer a series of questions specified by a particular government protocol, for example. At step 1334, in response to a detected file closing by the HCP, system 100 responds by updating the athlete's competition status to reflect that the athlete is now clear to return to play. Next, at step 1336, the updated status is attached to or associated with athlete's record and athlete's ID. Lastly, at step 1338, notice of the athlete's updated status is communicated by system 100 to interested parties such as the athlete, parents, coaches, league, primary care physician, and the like.

As described above, with the passage of time, system 100 will typically operate to build-up a comprehensive history of an athlete, potentially beginning at an early age and carrying through collegiate or even professional competition. This history may include both performance-related and health-related data, the latter being protected with appropriate confidentiality safeguards. Assuming that a statistically significant number of athletes register with the system, their aggregated records may be used to produce a wide variety of anonymous data sets of interest to researchers, government health agencies, physicians and therapists, and others.

The foregoing description has been directed to specific embodiments of this invention. It will be apparent, however, that other variations and modifications may be made to the described embodiments, with the attainment of some or all of their advantages. For example, it is expressly contemplated that the teachings of this invention can be implemented as software, including a computer-readable medium having program instructions executing on a computer, hardware, firmware, or a combination thereof. Accordingly this description is to be taken only by way of example and not to otherwise limit the scope of the invention. It is thus the object of the appended claims to cover all such variations and modifications as come within the true spirit and scope of the invention.

What is claimed is:

1. A system for managing participation of athletes in organized sports, said system comprising:
    one or more servers having network connectivity and arranged to provide cloud-based services, said cloud-based services including support for a public application and a physician application;
    said one or more servers having access to an athlete registry, said athlete registry storing an athlete record having a unique athlete identifier (ID) corresponding to each athlete that registers with said system;
    a permanent identification card for each registered athlete, said permanent identification card having non transitory machine-readable information including the unique athlete ID for the athlete who is identified by the permanent identification card;
    one or more machines each of which, in response to reading said non transitory machine-readable information, communicates with said one or more servers to determine in real-time, based on information stored in or associated with said athlete record, whether the registered athlete whose permanent identification card was read is cleared to participate in a predetermined sport;
    said public application communicating with said one or more servers so as to enable a public user to upload and download public information regarding one or more registered athletes; and
    said physician application communicating with said one or more servers so as to enable a physician to upload and download health-related information regarding one or more registered athletes, and to suspend one or more of said registered athletes from participating in said predetermined sport.

2. The system as in claim 1 wherein said physician application enables said physician to upload vital signs and pre-competition observations regarding one or more of said registered athletes.

3. The system as in claim 1 wherein said physician application enables said physician to report an injury to a registered athlete and generate a unique incident identifier (ID).

4. The system as in claim 3 wherein in response to report of an injury, said system automatically issues notifications to an injured athlete's family physician, sports league, medical provider, and overseeing body.

5. The system as in claim 1 wherein said physician application enables said physician to dictate observations and findings, and said system stores said dictation in encrypted form.

6. The system as in claim 1 wherein during registration or subsequently, a unique baseline identifier (ID) is obtained from a testing company that administered a baseline test to one of said registered athletes, and is added to or associated with the respective athlete record for the athlete that was tested.

7. The system as in claim 6 wherein each said unique baseline ID includes information identifying the testing company which administered the baseline test.

8. A method for managing participation of athletes in organized sports, said method comprising the steps of:
    providing a network cloud-based service including one or more servers having network connectivity which includes support for a public application and a physician application;
    establishing an athlete registry within said cloud-based service, said athlete registry storing an athlete record having a unique athlete identifier (ID) corresponding to each athlete that registers with said cloud-based service;
    issuing a permanent identification card for each registered athlete, said permanent identification card having non transitory machine-readable information including the unique athlete ID for the athlete who is identified by the permanent identification card;
    providing one or more machines each of which, in response to reading said non transitory machine-readable information, communicates with said cloud-based service to determine in real-time, based on information stored in or associated with said athlete record, whether the registered athlete whose permanent identification card was read is cleared to participate in a predetermined sport;
    using a public application to communicate with said cloud-based service to upload and download public information regarding one or more registered athletes; and
    using a physician application to communicate with said cloud-based service to upload and download health-related information regarding one or more registered athletes, and to suspend one or more of said registered athletes from participating in said predetermined sport.

9. The method as in claim 8 wherein said physician application is used to upload vital signs and pre-competition observations regarding one or more of said registered athletes.

10. The method as in claim 8 wherein said physician application is used to report an injury to a registered athlete and generate a unique incident identifier (ID).

11. The method as in claim 10 wherein in response to report of an injury, said cloud-based service automatically issues notifications to an injured athlete's family physician, sports league, medical provider, and overseeing body.

12. The method as in claim 8 wherein said physician application is used to dictate observations and findings, and said cloud-based service stores said dictation in encrypted form.

13. The method as in claim 8 wherein during registration or subsequently, a unique baseline identifier (ID) is obtained from a testing entity which administered a baseline test to one of said registered athletes, and adding or associating said unique baseline ID with the athlete record for the athlete that was tested.

14. The method as in claim 13 wherein each said unique baseline ID includes information identifying the testing entity which administered the baseline test.

15. A method providing controlled access to health-related information, said method comprising the steps of:
    providing a network cloud-based service including one or more servers having network connectivity which includes support for a physician application;
    establishing an athlete registry within said cloud-based service, said athlete registry storing an athlete record having a unique athlete identifier (ID) corresponding to each athlete that registers with said cloud-based service;

determining, during or subsequent to registration, whether an athlete has taken a baseline test and if so, obtaining a unique baseline identifier (ID) from a testing company which administered the baseline test, said unique baseline ID including information sufficient to identify the testing company;

adding or associating said unique baseline ID with the athlete record of the athlete who was tested;

using said physician application to report an injury to one of said registered athletes and in response creating a unique incident identifier (ID) which is added to or associated with the athlete record of the injured registered athlete;

determining, based on the presence or absence of a unique baseline ID, whether the injured registered athlete was previously administered a baseline test and if so, transmitting a message to the testing company which includes the unique incident ID and information regarding a medical data destination location (MDDL) maintained within the cloud-based service;

receiving from the testing company an encrypted file contain baseline test results and storing said file in the MDDL;

transmitting a message to the injured registered athlete's health care provider (HCP) which includes the location of the MDDL, the unique athlete ID for the injured registered athlete, the unique baseline ID, and the unique incident ID; and requiring that the HCP possess all of the unique athlete ID for the injured registered athlete, the unique baseline ID, and the unique incident ID, in order to access the file containing the baseline test results stored in the MDDL.

16. The method as in claim 15 wherein said MDDL is a quarantined, secure directory maintained by said cloud-based service.

17. The method as in claim 15 wherein said MDDL is monitored for a file closing which indicates that the HCP has cleared the injured registered player to return to play.

18. The method as in claim 17 wherein said cloud-based service automatically issues notifications to preselected third parties that injured registered athlete is cleared to return to play.

19. The method as in claim 15 wherein if an expected file containing baseline test results is not received at the MDDL within a predetermined period of time, transmitting a reminder message to the testing company.

* * * * *